(12) United States Patent
Neumann et al.

(10) Patent No.: US 8,345,228 B2
(45) Date of Patent: Jan. 1, 2013

(54) MEASURING DEVICE AND METHOD FOR DETERMINING OPTICAL CHARACTERISTIC VARIABLES FOR VERIFYING PHOTOCHEMICAL AND ELECTROCHEMICAL DEGRADATIVE REACTIONS

(75) Inventors: Frank Neumann, Braunschweig (DE); Thomas Neubert, Braunschweig (DE); Michael Vergöhl, Destedt (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 386 days.

(21) Appl. No.: 12/665,361

(22) PCT Filed: Jun. 25, 2007

(86) PCT No.: PCT/EP2007/005606
§ 371 (c)(1),
(2), (4) Date: Feb. 24, 2010

(87) PCT Pub. No.: WO2009/000293
PCT Pub. Date: Dec. 31, 2008

(65) Prior Publication Data
US 2010/0182590 A1    Jul. 22, 2010

(51) Int. Cl.
*G01N 21/00* (2006.01)
(52) U.S. Cl. ............ 356/73; 356/72; 356/317; 356/417
(58) Field of Classification Search ............ 356/72, 356/73, 317, 417
See application file for complete search history.

(56) References Cited

U.S. PATENT DOCUMENTS

| | | | |
|---|---|---|---|
| 5,453,841 A | 9/1995 | Reipa et al. | |
| 7,499,154 B2 * | 3/2009 | Stock et al. | 356/73 |
| 2004/0206915 A1 | 10/2004 | Matsumura et al. | |

FOREIGN PATENT DOCUMENTS

| | | |
|---|---|---|
| DE | 102004027118 A1 | 12/2005 |
| DE | 102005003878 B3 | 7/2006 |
| DE | 102005011219 A1 | 9/2006 |
| DE | 102006049009 B3 | 6/2008 |
| JP | 2000162129 A | 6/2000 |
| JP | 2003294633 A | 10/2003 |
| JP | 2004138387 A | 5/2004 |
| WO | 2005119220 A1 | 12/2005 |

OTHER PUBLICATIONS

International Preliminary Examination Report for corresponding PCT application PCT/EP2007/005606, Feb. 11, 2010. (PCT/IB/338/IPEA/409)).
International Search Report for Corresponding PCT application PCT/EP2007/005606, Apr. 17, 2008. (PCT/ISA/220/210).
Written Opinion for Corresponding PCT application PCT/EP2007/00560, Apr. 17, 2008. (PCT/ISA/237).
J.T. Remillard, et. al., "Real Time in Situ Spectroscopic Ellipsometry Studies of the Photocatalytic Oxidation of Stearic Acid on Titania Films" J. Phys. Chem. B. 2000, 104, 4440-4447.
Office Action for corresponding Application JP 2010-513660, dated Nov. 2, 2011.

* cited by examiner

*Primary Examiner* — Layla Lauchman
(74) *Attorney, Agent, or Firm* — Matthew B. Dernier, Esq.; Gibson & Dernier LLP

(57) ABSTRACT

A measuring device for quantitative determination of optical characteristic values for detecting photo- and/or electrochemical decomposition reactions taking place on surfaces of photocatalytically active substrates.

31 Claims, 1 Drawing Sheet

MEASURING DEVICE AND METHOD FOR DETERMINING OPTICAL CHARACTERISTIC VARIABLES FOR VERIFYING PHOTOCHEMICAL AND ELECTROCHEMICAL DEGRADATIVE REACTIONS

FIELD OF THE INVENTION

The invention relates to a measuring device for quantitative determination of optical characteristic values for detecting photo- and/or electrochemical degradative reactions taking place on surfaces of photocatalytically active substrates. The invention hence describes a measuring device which makes it possible, during irradiation, to implement quantitative measuring methods for determining light-induced electrochemical degradative reactions, e.g. photocatalysis, in a sample chamber so that the efficiency of the irradiated samples can be determined both qualitatively and quantitatively in a measuring stage. It is thereby possible to detect optically different degradative reactions, e.g. photocatalytic decomposition of stearic acid, organic colourants or colourant-containing algal and bacterial strains, in parallel or individually during the activation without thereby requiring to change the measuring geometry or the arrangement of the samples relative to each other. For this purpose, the photo- or electrochemical excitation of the samples, i.e. the illumination, and also the generation and detection of the measuring signal is effected, e.g. by scattered light, by fluorescence, in situ via light sources which are separated from each other spectrally. The invention likewise relates to a corresponding method for detecting photo- and electrochemical degradative reactions. The measuring device is used in quantifying the photocatalytic activity of substrates.

BACKGROUND

The increasing development of industrial mass-produced parts with photocatalytically active, self-cleaning and antibacterial properties demands ever more precise, more rapid and more automated measuring methods. In the past, new measuring methods were thus developed with which it is possible to examine the surfaces of photocatalytic materials made of glass, plastic material, metal, wood or even textile woven fabrics for their self-cleaning and/or antibacterial properties during irradiation with UV light and also with light of the visible spectrum. Whilst the most current but easy to handle methods based on transmission- or absorption measurements of coloured aqueous solutions (e.g. methylene blue decomposition; DE 10 2005 011 219) deliver generally only qualitative results with very long measuring times, the precise application of thin layers of organic test substances directly on the surfaces makes possible extremely rapid and above all also quantitative evaluation of the photocatalytic activity.

DE 10 2004 027 118 describes a method for quantitative determination of the photocatalytic decomposition of organic colourants or colourant-containing algal and bacterial strains on photocatalytically active surfaces by means of fluorescence analysis. For this purpose, the samples to be tested are coated with organic colourants or colourant-containing substances. Subsequently, the samples are irradiated with UV or visible light of known intensity and spectral distribution and their fluorescence intensity is detected by means of fluorescence scanners, chip readers or a fluorescence microscope. The thereby resulting reduction in fluorescence of the colour-coated photocatalyst in comparison with a jointly coated but photocatalytically inactive reference thereby applies as a measure of the photocatalytic efficiency of the sample to be tested.

DE 10 2006 049 009.6 describes a measuring method for measuring the photocatalytic activity of surfaces by scattered light measurement on thin fatty acid layers. For this purpose, the surfaces to be measured are evaporated with thin stearic acid layers, as a result of which a homogeneous scattering surface is produced. The surface is subsequently irradiated with UV light and the light component scattered by the stearic acid layer (haze) is thereby measured at defined time intervals. If the surface is photocatalytically active, then the applied layer decomposes without residue so that the optical haze drops to the value of the uncoated surface. From the time-dependent curve course of the optical haze, the quantitative photocatalytic activity of the sample can hence be determined.

In contrast to other known photocatalytic measuring methods, DE 10 2004 027 118 and DE 10 2006 049 009 describe two novel measuring principles with a high throughput and with simultaneously high precision, as a result of which firstly exact and reproducible, quantitative determinations of the photocatalytic efficiency of different photocatalytically active surfaces could be produced with low complexity. Both methods hereby use different test substances (e.g. fluorescent colourants or organic fatty acids) so that different optical aids are required for acquiring the measuring values in the individual case. Whilst in fluorescence measurement of colourants, fluorescence scanners, chip readers or fluorescence microscopes can be used, there are required for scattered light measurement on the stearic acid layers, a haze meter, a gloss measuring device or a spectral photometer with connected integration sphere. Because of the different measuring geometries or the light sources required for the measurement, both methods cannot hence readily be combined with each other. Furthermore, according to the current state of research, no commercially available device is in a position to produce a quantitative analysis of photocatalytic activity with simultaneous irradiation in the UV or visible spectral range.

SUMMARY OF THE INVENTION

Starting herefrom, it was the object of the present invention to provide a measuring device which combines different optical determination methods with minimum technical complexity in order to enable rapid quantitative photocatalytic analysis of different samples without the series of measurements of the different methods which are implemented in parallel or in succession being mutually influenced. Manipulation or impairment of the measuring results by external influences, e.g. parasitic illuminations or activation of the samples, is intended thereby to be precluded so that the photocatalytic efficiency of active surfaces can be determined precisely.

This object is achieved by the measuring device having the features disclosed herein and by the method having the features disclosed herein.

BRIEF DESCRIPTION OF THE DRAWINGS

The subject according to the application is now intended to be explained in more detail with reference to the subsequent FIG. 1 without wishing to restrict said subject to the special embodiments shown here.

DETAILED DESCRIPTION OF THE INVENTION

Figure 1A:
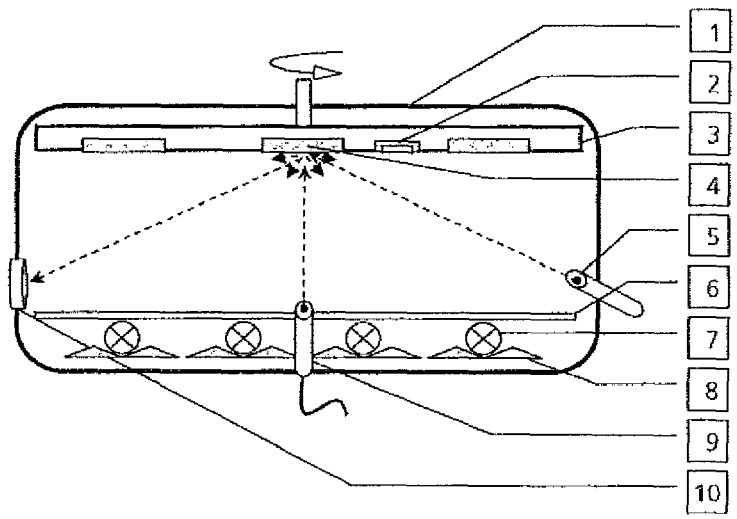
FIG. 1a) shows a side view of a measuring device according to the invention.
Figure 1B:
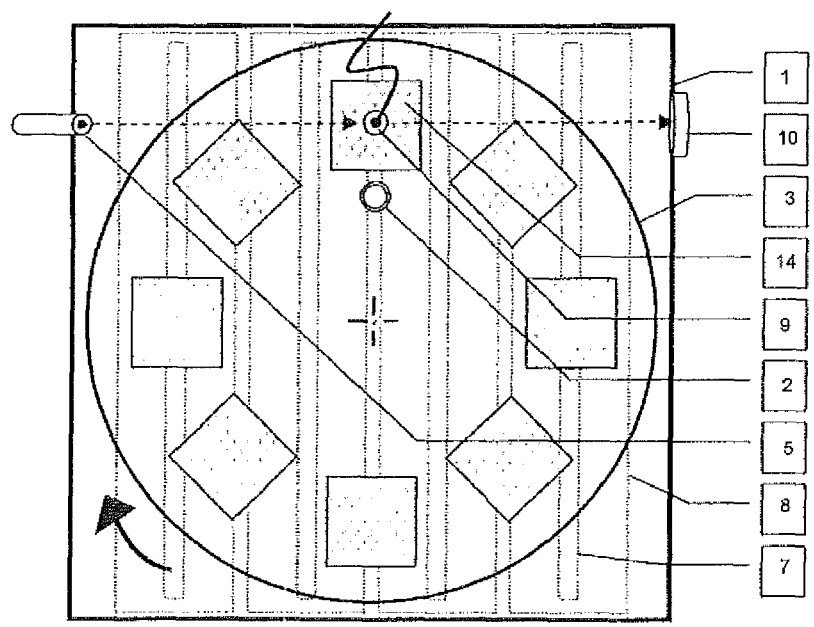
FIG. 1b) shows a plan view from above of a measuring device according to the invention. The elements corresponding to FIG. 1a) are represented in FIG. 1b) in plan view.

According to the invention, a measuring device is provided for quantitative determination of optical characteristic values of photo- and/or electrochemical degradative reactions taking place on surfaces of photocatalytically active substrates. This measuring device comprises the following components integrated in one housing:
 a) a mounting device for at least one substrate to be examined,
 b) at least one activation radiation source for activation of the substrate,
 c) at least one measuring radiation source for generating scattered light on the substrate and/or for fluorescence excitation of the substrate, and also
 d) at least one detector for quantifying scattered light and/or fluorescence.

The measuring device according to the invention thereby has the following advantages.

Different photocatalytic measuring methods (scattered light measurement and fluorescence analysis) can be combined in one device, as a result of which a rapid, precise, quantitative analysis of the irradiated samples is made possible.

The activation of the samples is effected with irradiation with UV light (200 nm<$\lambda$<400 nm) and also with light of the visible spectrum ($\lambda$>400 nm).

The irradiation for activation of the samples and also the illumination for measuring the samples by means of scattered light or fluorescence excitation is however effected simultaneously with separate light sources of different wavelength ranges in order to preclude mutual influencing.

The optical measurement of the samples is effected in reflection so that, in addition to glass and plastic material, also samples made of opaque materials, such as ceramic, wood or steel and the like, with different surface geometries or roughnesses can be detected.

The measuring stages are effected automatically; they can be implemented, according to the embodiment, simultaneously or successively with both methods or individually on the same samples.

When the irradiation intensity is known, the photocatalytic efficiency of the measured samples can be determined with both methods rapidly and absolutely.

If required, the measurements can be implemented in an air-conditioned environment in order to avoid temperature and air humidity variations.

As activation radiation source, the operation can take place both with virtually monochromatic sources, e.g. black light tubes, lasers or laser-LEDs, sources with a defined line spectrum, e.g. mercury vapour lamps, and sources with broadband spectral excitation, e.g. halogen lamps or daylight lamps. The spectral distribution of the light sources and also the illumination strength thereof is intended preferably to be controllable if required, preferably in a range between 0 to 10 mW/cm$^2$. It is likewise advantageous if the intensity of the light sources which are used can be detected photometrically in parallel to the measurement.

It is hereby advantageous, for measurement of the samples, to use light of higher wavelength ranges than is required for activation of the samples in order both to separate signals from each other and to avoid parasitic illuminations. The measurement of the samples can thus be effected by means of scattered light or fluorescence with simultaneous activation with UV-C- (200-280 nm), UV-B- (280-320 nm), UV-A- (320-400 nm) or visible light up to maximum 450 nm (corresponding to a bandgap of approx. 2.75 eV) with a single monochromatic light source, e.g. laser-LED, the wavelength of which is at least the same or greater than the maximum wavelength of the light used for activation of the samples. However, the photon energy of the measuring light must hereby be constantly smaller than the bandgap of the photocatalyst to be examined in order to avoid an additional photocatalytic excitation of the sample. Furthermore, it is advantageous to adapt the wavelength of the monochromatic light source used for the measurement to the absorption characteristic of the organic test substances to be decomposed in order to ensure optimum fluorescence excitation or optimum scattering of the thin layers. Thus the wavelength of this light source should be between 450 nm (blue) to 850 nm (red), preferably between 450 nm to 650 nm and particularly preferred between 470 nm and 532 nm (green) since neither an additional activation of the samples in the shortwave nor undesired thermal heating in the longwave is effected here.

If the samples to be examined are disposed during the irradiation on a rotating sample plate or a linearly moving sample table, both measuring methods can be combined on the one point of the sample plate trajectory or on a line central to the axis of movement of the sample plate since both methods use the same light source for measuring the samples in reflection. The monochromatic light used to measure the samples is hereby either scattered on the sample surface coated with stearic acid or it can excite colourant deposited on the surface to fluorescence. Both measuring methods can hence be implemented simultaneously, successively or separately from each other on respectively the same samples. However, it is also adequate for specific sample geometries if the device is equipped optionally only with one of the two measuring methods in order to carry out a quantitative analysis.

Whilst the samples are irradiated on the layer side with perpendicular incidence by means of UV radiation or visible light of known intensity, the scattered light measurement of the samples ideally is effected at an angle of incidence of 45°±40° relative to the sample normal, whilst the fluorescence is determined via an optical fibre, a CCD camera or a photodiode likewise perpendicular to the sample surface. The recording of the measuring values can thereby be effected in a stationary manner on a sample or triggered as a function of the positioning speed of the sample plate on various samples in succession. The processing and output of the measuring results and also the triggering and control of the components located in the device (light sources, sample plates etc.) can in addition be effected in the device itself or via a periphery adjoining the device, e.g. laptop, PC.

Furthermore, it is advantageous to mount the sample to be examined headfirst with the layer side at the bottom on a sample holder provided with openings and to irradiate and measure it also from the bottom. As a result, even with thicker samples, a constant measuring or irradiation spacing can always be ensured without requiring to adapt the sample holder, the illumination sources or the measuring optical system to each other at a spacing. However, a measuring construction is also conceivable with sample at the bottom and layer side at the top and irradiation or measuring optical system disposed thereabove. In a further embodiment, the irradiation can also be implemented separately from the evaluation optical system in a chamber separated by light traps in the device, however the samples must thereby be supplied several times at specific time intervals to the measuring optical systems, which results in a corresponding discontinuity of the measurement and irradiation of the respective samples. In addition, it is advantageous for all embodiments to air-condition the irradiation chamber sufficiently in order to preclude falsifications of the measuring values as a result of temperature and air humidity variations.

Independently of the respective measuring method, the time-dependent reduction in scattering or fluorescence intensity of the irradiated samples applies as a measure of the effectiveness of the photocatalytic surface for all embodiments. Determination of the photocatalytic efficiency of the samples can be effected subsequently according to the principles mentioned in DE 10 2004 027 118 and DE 10 2006 049 009.

According to the invention, a method is likewise provided for quantitative determination of optical characteristic values for detecting photo- and/or electrochemical degradative reactions taking place on surfaces of photocatalytically active substrates, in which
 a) a substrate to be examined is coated on at least one surface with a substance which can decompose as a result of photo- and/or electrochemical degradative reactions,
 b) the surface coated with the substance is activated by irradiation with an activation radiation source,
 c) before, simultaneously and/or subsequently to step b), the surface of the substrate coated with the substance is irradiated at least once with light originating from a measuring radiation source, and
 d) the temporal decomposition of the substance is measured via the scattered light of the measuring radiation source which is emitted by the surface of the substrate and/or via the fluorescence.

The measuring devices according to the invention are used in the quantification of photocatalytic activity of substrates. The substrates can hereby be selected from the group consisting of carrier structures which are coated with at least one metal oxide, in particular titanium oxide, niobium oxide, vanadium oxide or zinc oxide, a metal complex comprising at least one metal oxide, in particular titanium oxide, niobium oxide, vanadium oxide or zinc oxide with portion of any transition metals or at least one doped metal oxide with C, F, N or S as dopants, glass, in particular quartz glass or borosilicate glass, ceramic, metal, plastic materials, wood and/or paper.

The measuring device is applied furthermore in the analytical observation of optical changes of organic layers as a result of chemical reactions, e.g. oxidation and/or crystallisation.

The measuring device according to the invention, according to FIG. 1a), has a radiation-resistant housing with door or cover as irradiation chamber 1. A photosensor 2 for measuring and controlling the radiation intensity is disposed at the level of the sample surface. The mounting device 3 can be configured as a rotary plate or sample table with linear operation and serves for receiving the sample 4. Furthermore, the housing has a stable monochromatic light source 5 directed towards the sample surface for scattered light measurement or fluorescence excitation of the irradiated samples. On the opposite side of the housing, a photodiode 10 for detecting the scattered light intensity on the sample surface is disposed opposite the light source at the same angle and spacing.

Furthermore, the housing contains a filter 6 for screening out higher orders or undesired wavelength ranges. Activation radiation sources 7 comprising fluorescent tubes, halogen, black or daylight lamps are disposed perpendicular to the surface. These can also be combined with a reflector 8. The housing likewise has a fibre optic 9 orientated perpendicular to the sample surface with connected spectral fluorometer for detecting the fluorescence intensity of the irradiated samples. Furthermore, the housing can be supplemented by fans for heat dissipation or an air-conditioning unit for controlling the temperature and air humidity during measurement. As a further alternative, the housing can have a webcam directed towards the measuring spot for observing the sample and also a timer as end switch-off.

The invention claimed is:

1. A measuring device for quantitative determination of optical characteristic values for detecting photo- and/or electrochemical degradative reactions taking place on surfaces of photocatalytically active substrates, comprising the following components integrated in one housing:
 a) a mounting device for at least one substrate to be examined,
 b) at least one activation radiation source for activation of the substrate,
 c) at least one measuring radiation source for generating scattered light on the substrate and/or for fluorescence excitation of the substrate,
 d) at least one detector for quantifying scattered light and/or fluorescence, and
 e) at least one optical filter operating to effect separation of respective wavelength ranges of the activation radiation source and the measuring radiation source by at least 1 nm.

2. A measuring device according to claim 1, wherein the mounting device is a sample plate.

3. A measuring device according to claim 1 wherein the at least one activation radiation source emits radiation with a wavelength between 200 and 450 nm.

4. A measuring device according to claim 1 wherein the at least one activation radiation source is selected from the group consisting of black light tubes, halogen lamps, daylight lamps, mercury vapour lamps, lasers and/or laser LEDs.

5. A measuring device according to claim 1 wherein the at least one activation radiation source is disposed such that the radiation emitted by it impinges essentially perpendicularly on the mounting device.

6. A measuring device according to claim 1 comprising at least one activation radiation source which emits non-homogeneous radiation and, on a side of the at least one activation radiation source which is orientated away from the mounting device, at least one reflection element for homogenisation of the radiation emitted by the at least one activation radiation source in the direction of the mounting device.

7. A measuring device according to claim 1 wherein the at least one activation radiation source is configured as an array of several of equidistantly disposed activation radiation sources.

8. A measuring device according to claim 1 wherein the measuring radiation source emits radiation with a wavelength between 450 and 850 nm.

9. A measuring device according to claim 1 wherein the measuring radiation source is a monochromatic radiation source.

10. A measuring device according to claim 1 wherein the measuring radiation source is placed in the housing such that the radiation emitted by it impinges on the surface of the substrate at an angle of $45°\pm40°$ with respect to the normal to the substrate surface.

11. A measuring device according to claim 1 wherein the at least one detector is a photodiode for detecting scattered light.

12. A measuring according to claim 11, wherein the at least one detector is disposed with respect to the surface of the substrate essentially at the same angle and spacing as the measuring radiation source and also situated opposite the measuring radiation source.

13. A measuring device according to claim 11 wherein the at least one detector is disposed at an angle of 45°±40° with respect to the normal to the substrate surface.

14. A measuring device according to claim 1 wherein at least one further detector is present for detecting the fluorescence of the substrate.

15. A measuring device according to claim 14, wherein the detector is selected from the group consisting of CCD sensors and spectrometers.

16. A measuring device according to claim 1 wherein the at least one optical filter operates to effect separation of the respective wavelength ranges of the activation radiation source and the measuring radiation source by at least 10 nm.

17. A measuring device according to claim 1 further comprising a photosensor for measuring the radiation intensity impinging on the substrate.

18. A measuring device according to claim 17, wherein the photosensor of the activation radiation source is fitted essentially at the same spacing as the substrate.

19. A measuring device according to claim 18, wherein the the photosensor is integrated in the mounting device.

20. A measuring device according to claim 1 further comprising a device for air-conditioning of the interior of the housing.

21. A measuring device according to claim 1 further comprising a camera for observing the substrate.

22. A measuring device according to claim 1 further comprising a timer for controlling a measuring duration of the measuring device.

23. A method for quantitative determination of optical characteristic values for detecting photo- and/or electrochemical degradative reactions taking place on surfaces of photocatalytically active substrates with the measuring device according to claim 1 comprising
   a) coating at least one surface of a substrate to be examined with a substance which can decompose as a result of photo- and/or electrochemical degradative reactions,
   b) activating the surface coated with the substance by irradiation with the activation radiation source,
   c) irradiating, before, simultaneously and/or subsequently to step b), the surface of the substrate coated with the substance at least once with light originating from the measuring radiation source, and
   d) measuring a temporal decomposition of the substance via the scattered light of the measuring radiation source which is emitted by the surface of the substrate and/or via the fluorescence.

24. The method according to claim 23 wherein the decomposable substance is selected from the group consisting of vaporisable organic substances, organic colourants, organic fatty acids and derivatives thereof.

25. The method according to claim 23 wherein the substance is vapour-deposited, sprayed, imprinted, coated with a doctor knife on the substrate and/or applied by immersion of the substrate in a solution of the substance.

26. The method according to claim 23 wherein the substance is applied in a thickness of 1 to 1,000 nm.

27. The method according to claim 23, wherein the irradiation of the substrate effected in step b) and/or step c) is effected over a period of time of 1 min to 12 hours.

28. The method according to claim 23, wherein the irradiation of the substrate is effected in step b) with an intensity of 0.1 mW/cm$^2$ up to and including 10 mW/cm$^2$ relative to the surface of the substrate.

29. The method according to claim 23 wherein the radiation used in step c) is longer-wave than the radiation used in step b).

30. A measuring device according to claim 1 operable for quantifying photocatalytic activity of substrates selected from the group consisting of carrier structures which are coated with a metal oxide, a metal complex comprising a metal oxide, glass, ceramic, metal, plastic, wood and paper.

31. A measuring device according to claim 1 operable for analytical observation of optical changes of organic layers as a result of chemical reactions.

* * * * *